US009604016B2

(12) United States Patent
Price et al.

(10) Patent No.: US 9,604,016 B2
(45) Date of Patent: Mar. 28, 2017

(54) BENT CAPILLARY TUBE AEROSOL GENERATOR

(75) Inventors: Shane Price, Weaver, AL (US); Evgeni Sychev, Oxford, AL (US); Marc D. Belcastro, Glen Allen, VA (US); Jeffrey A. Swepston, Powhatan, VA (US)

(73) Assignee: Philip Morris USA Inc., Richmond, VA (US)

( * ) Notice: Subject to any disclaimer, the term of this patent is extended or adjusted under 35 U.S.C. 154(b) by 2053 days.

(21) Appl. No.: 11/699,497

(22) Filed: Jan. 30, 2007

(65) Prior Publication Data

US 2007/0262478 A1 Nov. 15, 2007

Related U.S. Application Data

(60) Provisional application No. 60/763,350, filed on Jan. 31, 2006.

(51) Int. Cl.

| | |
|---|---|
| ***A61M 11/04*** | (2006.01) |
| ***A61M 15/00*** | (2006.01) |
| ***A61M 15/02*** | (2006.01) |

(52) U.S. Cl.

CPC ......... *A61M 11/041* (2013.01); *A61M 11/042* (2014.02); *A61M 15/025* (2014.02); *A61M 15/00* (2013.01); *A61M 2205/50* (2013.01); *A61M 2205/8206* (2013.01)

(58) Field of Classification Search

USPC ............. 128/200.11–200.14, 200.18–200.19, 128/200.21, 200.23–200.24, 128/203.12–203.17, 203.25–203.27, 128/204.17, 204.18, 204.21; 261/23.1, 261/23.2, 38, 39.1, 39.6, 64.1, 64.4, 78.1, 261/78.2; 239/418, 398, 338, 137, 136, 239/135; 392/200.11–200.14, 392/200.18–200.19, 200.21, 392/200.23–200.24, 465, 468, 469, 473, 392/478

See application file for complete search history.

(56) References Cited

U.S. PATENT DOCUMENTS

| | | | | |
|---|---|---|---|---|
| 2,998,640 A * | 9/1961 | Huet | ........................ | 29/890.051 |
| 5,411,208 A * | 5/1995 | Burgener | ........................... | 239/8 |
| 5,743,251 A | 4/1998 | Howell et al. | | |
| 6,134,387 A * | 10/2000 | Toss | .............................. | 392/478 |
| 6,234,402 B1 * | 5/2001 | Ganan-Calvo | .................... | 239/8 |

(Continued)

FOREIGN PATENT DOCUMENTS

WO WO 2007/102087 9/2007

OTHER PUBLICATIONS

International Search Report and Written Opinion dated Aug. 28, 2008 for PCT/IB2007/004497.

(Continued)

*Primary Examiner* — Rachel Young

(74) *Attorney, Agent, or Firm* — Buchanan Ingersoll & Rooney PC

(57) ABSTRACT

An apparatus for generating aerosol comprises a capillary tube comprising at least one bend, fluid inlets, and an outlet along the bend. The capillary tube is heated to a temperature sufficient to volatilize fluid in the capillary tube, such that the volatilized fluid discharges from the outlet to form an aerosol.

20 Claims, 5 Drawing Sheets

(56) References Cited

U.S. PATENT DOCUMENTS

| | | | | |
|---|---|---|---|---|
| 6,276,347 | B1 * | 8/2001 | Hunt | 123/549 |
| 6,491,233 | B2 | 12/2002 | Nichols | |
| 6,568,390 | B2 | 5/2003 | Nichols et al. | |
| 6,640,050 | B2 | 10/2003 | Nichols et al. | |
| 6,681,769 | B2 * | 1/2004 | Sprinkel et al. | 128/203.26 |
| 6,701,921 | B2 | 3/2004 | Sprinkel, Jr. et al. | |
| 6,701,922 | B2 | 3/2004 | Hindle et al. | |
| 6,715,487 | B2 | 4/2004 | Nichols et al. | |
| 6,766,220 | B2 | 7/2004 | McRae et al. | |
| 6,772,757 | B2 | 8/2004 | Sprinkel, Jr. | |
| 6,804,458 | B2 | 10/2004 | Sherwood et al. | |
| 6,854,461 | B2 | 2/2005 | Nichols et al. | |
| 6,871,792 | B2 | 3/2005 | Pellizzari | |
| 6,923,179 | B2 * | 8/2005 | Gupta et al. | 128/203.17 |
| 2003/0056790 | A1 | 3/2003 | Nichols et al. | |
| 2003/0106552 | A1 | 6/2003 | Sprinkel et al. | |
| 2003/0108342 | A1 | 6/2003 | Sherwood et al. | |
| 2003/0177768 | A1 * | 9/2003 | Pellizzari | 60/737 |
| 2004/0050383 | A1 | 3/2004 | Cox et al. | |
| 2004/0084050 | A1 * | 5/2004 | Baran | 128/207.14 |
| 2007/0262478 | A1 | 11/2007 | Price et al. | |

OTHER PUBLICATIONS

International Preliminary Report on Patentability and Written Opinion mailed Jul. 9, 2009 for International Application No. PCT/IB2007/004497.

International Preliminary Report on Patentability dated Aug. 14, 2008 for PCT/IB2007/001654.

International Search Report and Written Opinion dated Oct. 19, 2007 for PCT/IB2007/001654.

* cited by examiner

BENT CAPILLARY TUBE AEROSOL GENERATOR

CROSS REFERENCE TO RELATED APPLICATIONS

The present application claims priority under 35 U.S.C. 119 to U.S. Provisional Patent Application No. 60/763,350 filed on Jan. 31, 2006, the entire content of which is hereby incorporated by reference.

SUMMARY

Aerosols are useful in a wide variety of applications. For example, it is often desirable to treat respiratory ailments with, or deliver drugs by means of, aerosol sprays of finely divided particles of liquid and/or solid, e.g., powder, medicaments, etc., which are inhaled into a patient's lungs. Aerosols are also used for purposes such as providing desired scents to rooms, distributing insecticides and delivering paint, fuel and lubricant.

Provided is an aerosol generator in the form of a capillary tube, the capillary tube comprising at least one bend, fluid inlets, and an outlet along the bend, wherein volatilized fluid expands out of the outlet and mixes with ambient air to form an aerosol. The fluid inlets may be located at ends of the capillary tube. The capillary tube may comprise more than one bend, e.g., plural bends in the same plane or the tube may be coiled. The aerosol generator may comprise a source of liquid in fluid communication with the fluid inlets. The capillary tube may be 5 to 40 millimeters, preferably 10 to 25 millimeters, long and has an inner diameter of 0.1 to 0.5 millimeters, preferably 0.1 to 0.2 millimeters.

Also provided is an aerosol generator comprising a capillary tube comprising at least one bend, fluid inlets, and an outlet along the bend and a heating mechanism which heats the capillary tube to a temperature sufficient to volatilize fluid in the capillary tube. The capillary tube can be made of an electrically resistive heating material such as stainless steel and the heating mechanism can be a power supply with leads attached to the capillary tube to pass electrical current at least along the bend to heat the capillary tube to a temperature sufficient to volatilize fluid in the capillary tube. The aerosol generator may further comprise a mouthpiece and/or a source of fluid.

Further provided is a method for generating an aerosol, comprising the steps of supplying fluid to an aerosol generator comprising a capillary tube comprising at least one bend, first and second fluid inlets and an outlet along the bend and heating the capillary tube to heat the fluid to a temperature sufficient to volatilize the fluid to form a volatized fluid, such that the volatilized fluid expands out of the outlet of the capillary tube, the volatilized fluid mixing with ambient atmospheric air to form an aerosol. The outlet is preferably equidistant from the first and second fluid inlets. Fluid may be supplied to the first and second fluid inlets at identical or different flow rates. Identical or different fluids, which may be liquids, may be supplied to the first and second fluid inlets. A liquid may be supplied to a first fluid inlet and a gas may be supplied to a second fluid inlet. Fluid supplied to the capillary tube may comprise tobacco extracts and a carrier solution and/or at least one medicament.

DESCRIPTION OF THE PREFERRED EMBODIMENTS

Figure 1:
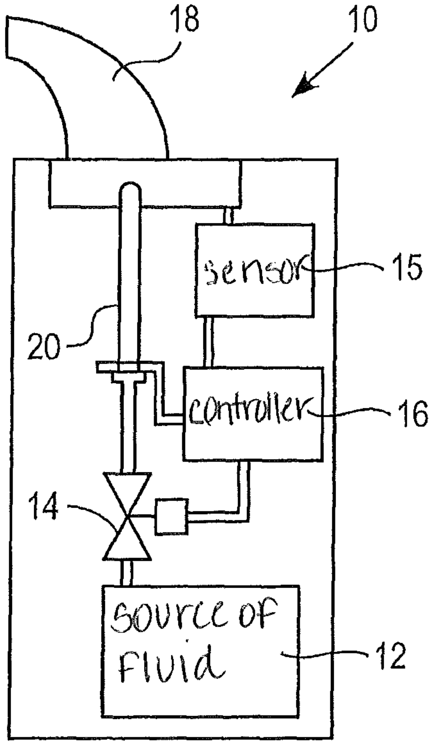
FIG. 1 is an illustration of a fluid vaporizing device.

Provided is a fluid vaporizing device useful for applications including aerosol generation. The device includes a bent capillary tube or passage which can be heated by passing electrical current therethrough, and through which fluid flows to be at least partially vaporized and if desired to generate an aerosol. Preferably, the bent capillary passage comprises an arcuate passage portion and an outlet at a location along the arcuate passage. In order to heat the tube, an electrical current supplied by a first electrode at one inlet end of the tube passes along the tube to a second electrode at the other inlet end of the tube. Fluid from the same or different sources can be supplied as a pressurized liquid at the inlets and is at least partially converted to a vapor by the input of heat generated by resistance heating from the flow of electricity along the tube as the fluid flows from the inlet ends through the tube toward the outlet. When used as an aerosol generator of an inhaler, such as a hand-held inhaler for aerosolizing medicaments or flavor substances, as the vapor exits from the tube at the outlet of the capillary tube an aerosol is produced as the vapor enters the surrounding atmosphere.

In a preferred embodiment, the bent capillary tube comprises at least one bend (or arcuate portion), such as a 180° bend, such that the inlet ends of the tube are equidistant from the outlet of the tube. Thus, as the bent capillary tube has more than one path (e.g., two legs) through which fluid travels from the inlets ends of the tube to the outlet, the bent capillary tube provides for a very compact structure compared to an aerosol generator comprising a linear capillary tube having a single path through which fluid travels from inlet to outlet. Further, compared to an aerosol generator comprising a capillary tube having a single path through which fluid travels from inlet to outlet, the pressure required to move fluid through the two legs of the bent capillary tube is lower to achieve a targeted flow rate. Conversely, for a targeted flow rate of aerosol, the flow rate of fluid traveling through each leg of the tube is slower. As a result of a slower flow rate of fluid traveling through the two legs of the tube, heat is transferred more efficiently from the tube into the fluid, less energy is required to vaporize (volatilize) liquid flowing through the tube, and the footprint of the tube may be reduced. Preferably, sufficient heat is transferred to vaporize all of the liquid entering the bent capillary by the time the fluid arrives at the outlet.

As the bent capillary tube has more than one inlet, an aerosol comprising more than one fluid may be formed. More specifically, different liquids, which may not mix well, may be fed into respective inlet ends of the tube. Alternatively, an aerosol comprising liquid and gas may be formed by feeding liquid into, for example, one inlet end of the tube and gas into, for example, the other inlet end of the tube. Further, a carrier solution containing tobacco extracts or tobacco flavor constituents may be used to form an aerosol, with the resulting aerosol having organoleptic attributes similar to tobacco smoke.

Preferably, the temperature of the tube and the fluid are greatest at the outlet and preferably, the outlet is at the center of the bend in the tube, (e.g., is preferably equidistant from each inlet end of the tube and preferably equidistant from each electrode), and the outlet preferably has a diameter approximately equal to the inner diameter of the bent capillary tube. However, if different fluids are fed into each inlet end of the tube, in order to optimize aerosol generation, it may be preferable that the outlet not be equidistant from each inlet end of the tube or equidistant from each electrode and/or the electrode not be located in identical positions on respective paths from the inlet ends of the tube to the outlet. Further, if different fluids are fed into each inlet end of the tube, in order to optimize aerosol generation, it may be preferable that the different fluids be fed at different flow rates.

The capillary tube can be made entirely from an electrically conductive material, such as stainless steel, so that as a voltage is applied to a length of the tube, the tube is heated by the flow of electrical current through the tube, and the fluid passing through the tube is vaporized. As an alternative, the tube could be made from a non-conductive or semi-conductive material, such as glass or silicon, with a coating or layer of resistance heating material such as platinum for heating the tube. Specifically, the tube could be fused silica with heater element formed by a resistive coating.

Provided is an improvement to a single capillary tube arrangement used to vaporize fluid wherein heat loss can occur at an electrical lead nearest the capillary tube exit and cause a dramatic decline in temperature along the capillary tube toward the tip. To compensate for such heat loss and maintain the tip at a temperature sufficiently high for the generation of a quality aerosol, the capillary midsection may be overheated. This overheating exposes the fluid to be aerosolized to unnecessarily high temperatures which can, in some cases, be sufficient to cause thermal degradation of fluid constituents.

FIG. 1 shows an embodiment of a fluid vaporizing device in the form of an aerosol generator 10 for use as a hand held inhaler. As shown, the aerosol generator 10 includes a source 12 of fluid, a valve 14, a heater arrangement comprising a bent (or hairpin) capillary tube 20, a mouthpiece 18, an optional sensor 15 and a controller 16. The controller 16 includes suitable electrical connections and ancillary equipment such as a battery which cooperates with the controller for operating the valve 14, the sensor 15 and supplying electricity to heat the bent capillary tube 20. In operation, the valve 14 can be opened to allow a desired volume of fluid from the source 12 to enter the bent capillary tube 20 prior to or subsequent to detection by the sensor 15 of a pressure drop in the mouthpiece 18 caused by a smoker/patient attempting to inhale aerosol from the aerosol generator 10. As fluid is supplied to the bent capillary tube 20, the controller 16 controls the amount of power provided to heat the capillary tube sufficiently to volatilize fluid in the bent capillary tube 20, i.e., the controller 16 controls the amount of electricity passed through the capillary tube to heat the fluid to a suitable temperature for volatilizing the fluid therein. The volatilized fluid exits an outlet of the bent capillary tube 20, and the volatilized fluid forms an aerosol which can be inhaled by a person upon his/her drawing upon the mouthpiece 18.

The aerosol generator shown in FIG. 1 can be modified to utilize different fluid supply arrangements. For instance, the fluid source can comprise a delivery valve which delivers a predetermined volume of fluid to the bent capillary tube 20 and/or the bent capillary tube 20 can include one or more metering chambers of predetermined size to accommodate a predetermined volume of fluid to be volatilized during an inhalation cycle. In the case where the bent capillary tube 20 includes one or more metering chambers to accommodate a volume of fluid, the device can include a valve or valves downstream of the chamber(s) for preventing flow of the fluid beyond the chamber(s) during filling thereof. If desired, the chamber(s) can include a preheater arranged to heat fluid in the chamber(s) such that a vapor bubble expands and drives the remaining liquid from the chambers into the bent capillary tube 20. Details of such a preheater arrangement can be found in commonly owned U.S. Pat. No. 6,491,233, the disclosure of which is hereby incorporated by reference. Alternatively, fluid in the chamber(s) could be preheated to a set temperature below vapor bubble formation. If desired, the valve(s) could be omitted and the fluid source 12 can include a delivery arrangement such as one or more syringe pumps which supply a predetermined volume of fluid directly to the bent capillary tube 20. In the case where the bent tube is made of an electrically conductive material such as stainless steel, the heating arrangement can be a portion of the capillary tube defining bent capillary tube 20, arranged to volatilize the liquid in bent capillary tube 20. The sensor 15 can be omitted or bypassed in the case where the aerosol generator 10 is operated manually by a mechanical switch, electrical switch or other suitable technique. Although the aerosol generator 10 illustrated in FIG. 1 is useful for aerosolization of inhalable aerosols, such as drug or flavor bearing aerosols, the bent capillary tube can also be used to vaporize other fluids such as, for example, odorants, insecticides, paint, lubricants, and fuels.

A bent capillary tube aerosol generator may receive fluid flow from a single fluid source. A fluid, generally in the form of a pressurized liquid and/or predetermined volume of fluid from the same or separate fluid sources, enters through the inlets of the capillary tube and flows through the legs of the tube towards the outlet of the tube. Preferably a separate electrode is provided at each inlet end of the capillary tube. The portion of the capillary tube between the electrodes is heated as a result of the electrical current flowing through a portion of the tube between the electrodes, and the liquid entering the inlet ends is heated within the tube to form a vapor. As the vapor exits from the outlet of the capillary tube and comes into contact with the surrounding ambient air, the vapor forms an aerosol. If the liquid is a suspension, the aerosol can be formed from solids in the suspension. If the liquid is a solution of a condensable liquid, the aerosol can be formed from droplets of condensed vapor. If the outlet is smaller in cross-section that the internal diameter of the capillary tube, the aerosol can be formed from atomized liquid driven through the outlet by vaporized liquid.

Figure 2:
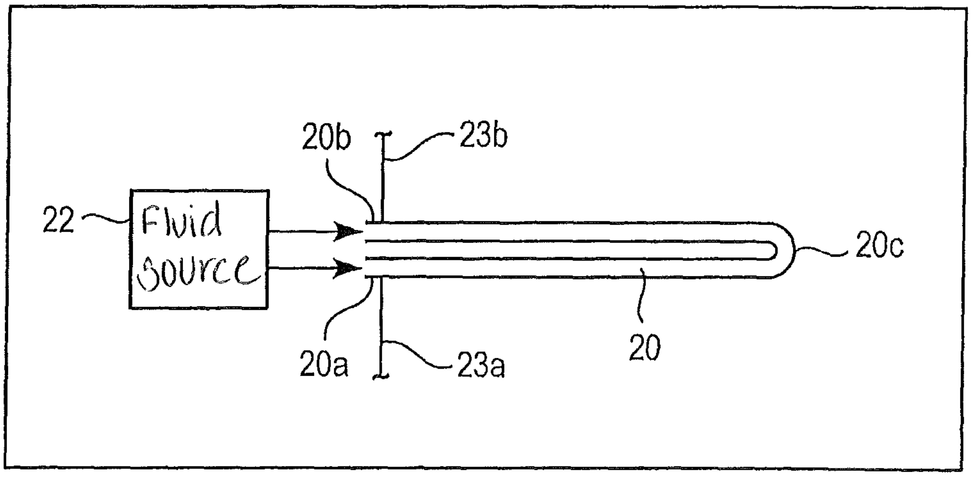
FIG. 2 is a schematic representation of a bent capillary tube portion of the device shown in FIG. 1.

As shown in FIG. 2, a fluid vaporizing device includes a capillary tube 20, with a fluid from a fluid source 22 passing through the capillary tube 20. The fluid enters the capillary tube 20 at first inlet end **20*a* and second inlet end 20*b*, and exits as a vapor from the outlet 20***c* of capillary tube 20. A first electrode 23*a* is connected near the inlet end 20*a* of capillary tube 20, and a second electrode 23*b* is connected near the inlet end 20*b*.

A liquid entering at the inlet 20*a* of capillary tube 20 and inlet 20*b* is heated as it passes through the capillary tube. Sufficient heat is input to the fluid passing through the tube to vaporize at least some of the fluid as it exits from the outlet 20*c* of the capillary tube. Again, while not illustrated but as indicated above, the aerosol generator may include more than one fluid source for each inlet of the bent capillary tube.

Figures 3A, 3B, 3C:
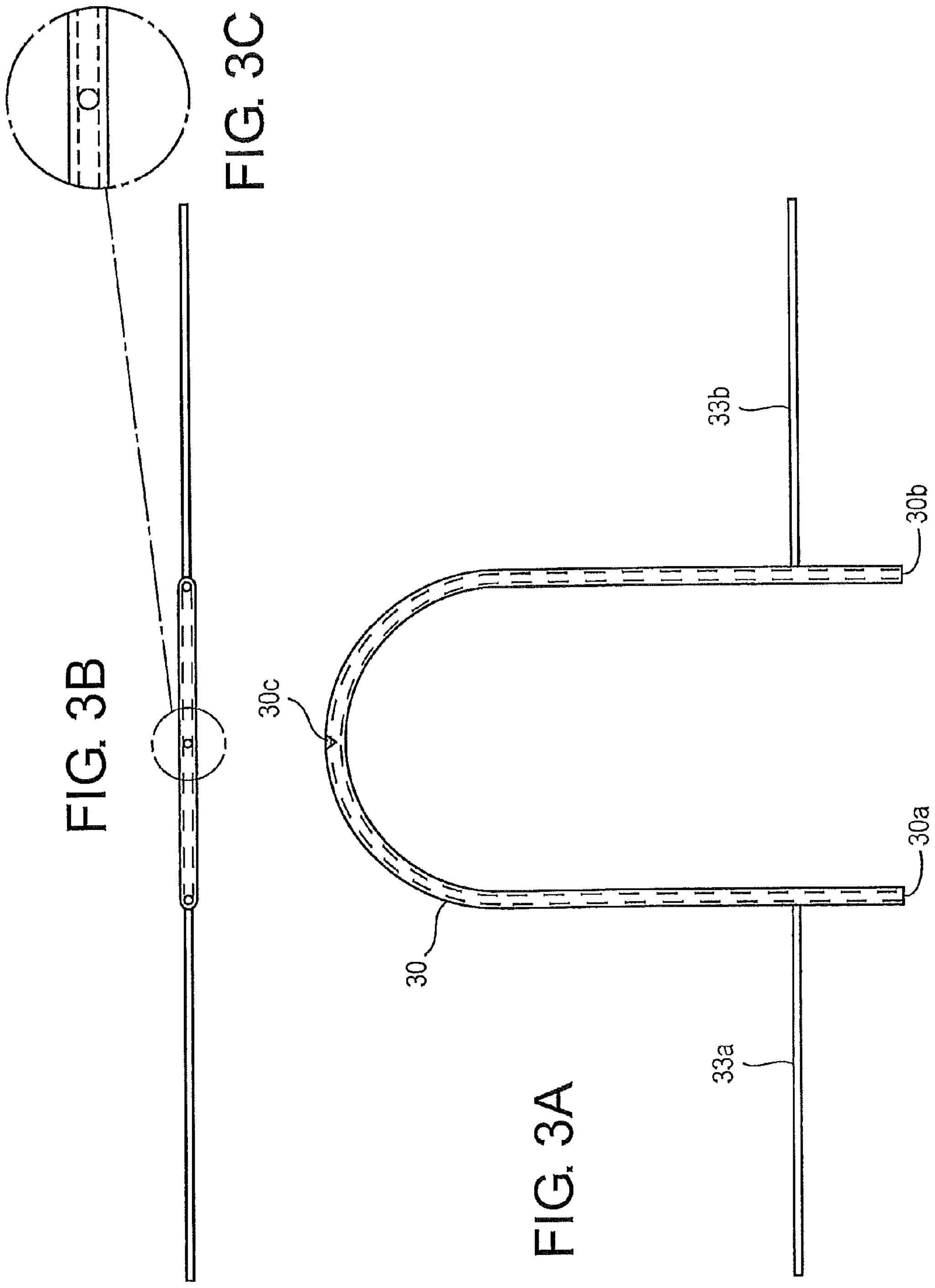
FIG. 3 provides an enlarged view of the bent capillary tube, with FIG. 3*a* providing a front view, FIG. 3*b* providing a top view, and FIG. 3*c* providing a magnified view of the outlet of the capillary tube.

FIGS. 3*a-b* illustrate an enlarged view of the bent capillary tube 30. FIG. 3*a* provides a top view of the bent capillary tube 30, in which fluid enters at first inlet end 30*a* and second inlet end 30*b*, and exits as a vapor from the outlet 30*c* in a semicircular bend in capillary tube 30. A first electrode 33*a* is connected near the inlet end 30*a* of capillary tube 30, and a second electrode 33*b* is connected near the inlet end 30*b*. FIG. 3*b* illustrates a front view of the bent capillary tube, and FIG. 3*c* provides a magnified view of the outlet of the capillary tube.

Figure 4C:
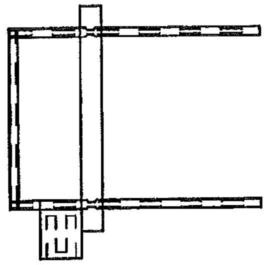
FIGS. 4*a-c* provide perspective views of the bent capillary tube connected to and extending through an electronics driver printed circuit card with a controller, with FIG. 4*a* providing a front view, FIG. 4*b* providing a side view, and FIG. 4*c* providing a top view.
Figure 4A:
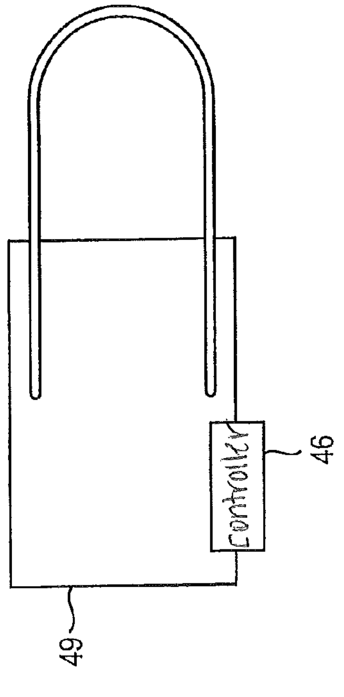
Figure 4B:
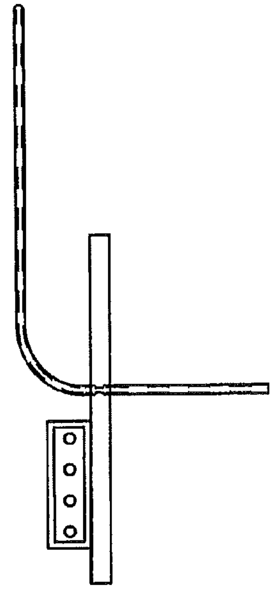

FIGS. 4*a-c* illustrate perspective views of the bent capillary tube. Specifically, FIG. 4*a* provides a top view of the bent capillary tube, which is connected to and extends through the electronics driver printed circuit card 49 with a controller 46, FIG. 4*b* provides a side view of the bent capillary tube, which is connected to the electronics driver printed circuit card and controller, and FIG. 4*c* provides a front view of the bent capillary tube, which is connected to the electronics driver printed circuit card and controller. The legs of the bent capillary tube are preferably connected to the electronics driver printed circuit card by a conductive adhesive, such as, for example, solder or conductive epoxy, allowing the electronics driver printed circuit card to supply electricity to the legs of the bent capillary tube to heat the bent capillary tube.

Figure 5:
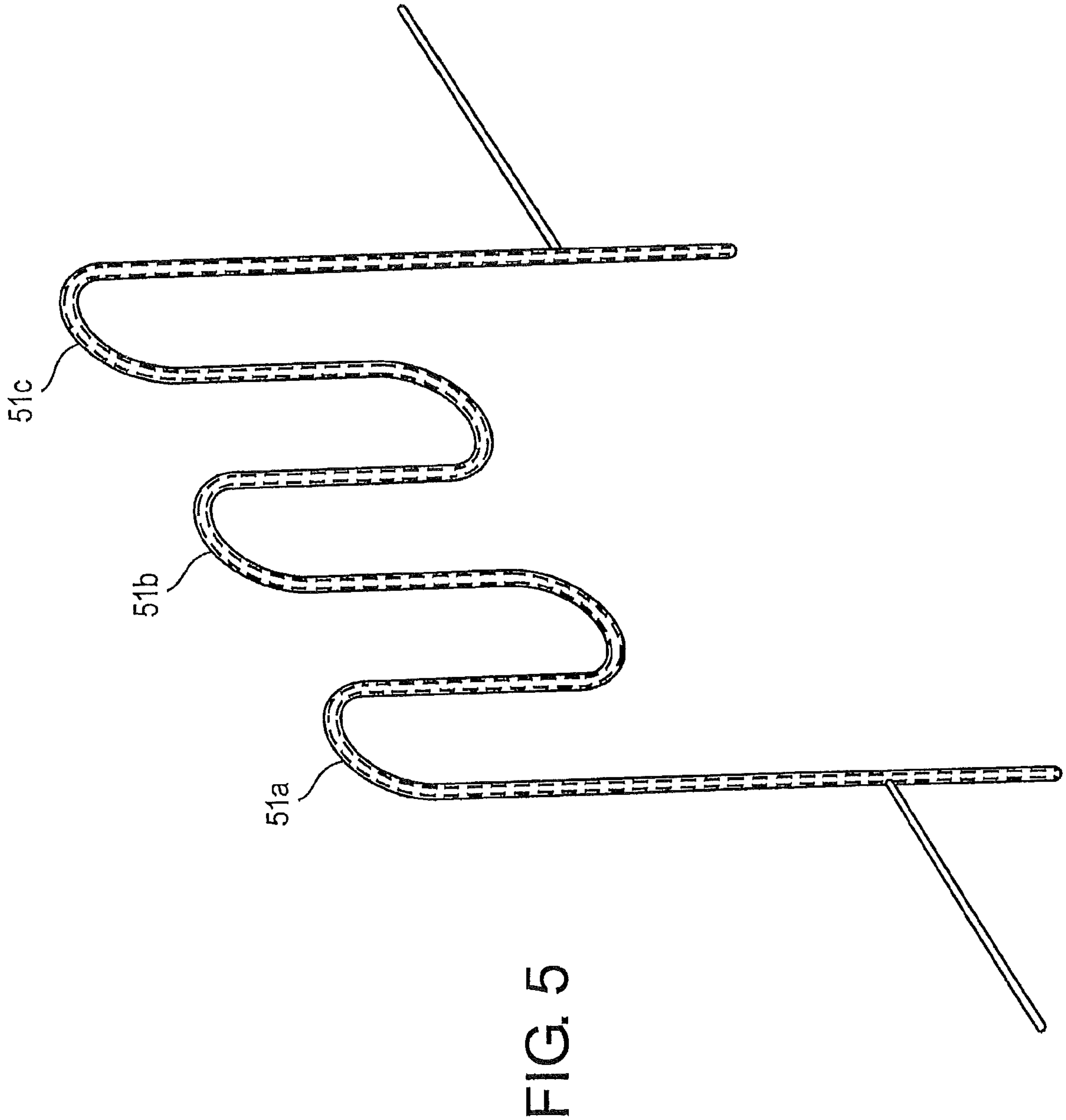
FIGS. 5 and 6 show additional embodiments of the bent capillary tube. The bent capillary tube of FIG. 5 includes multiple bends and the bent capillary tube of FIG. 6 includes a coiled tube having multiple bends.
Figure 6:
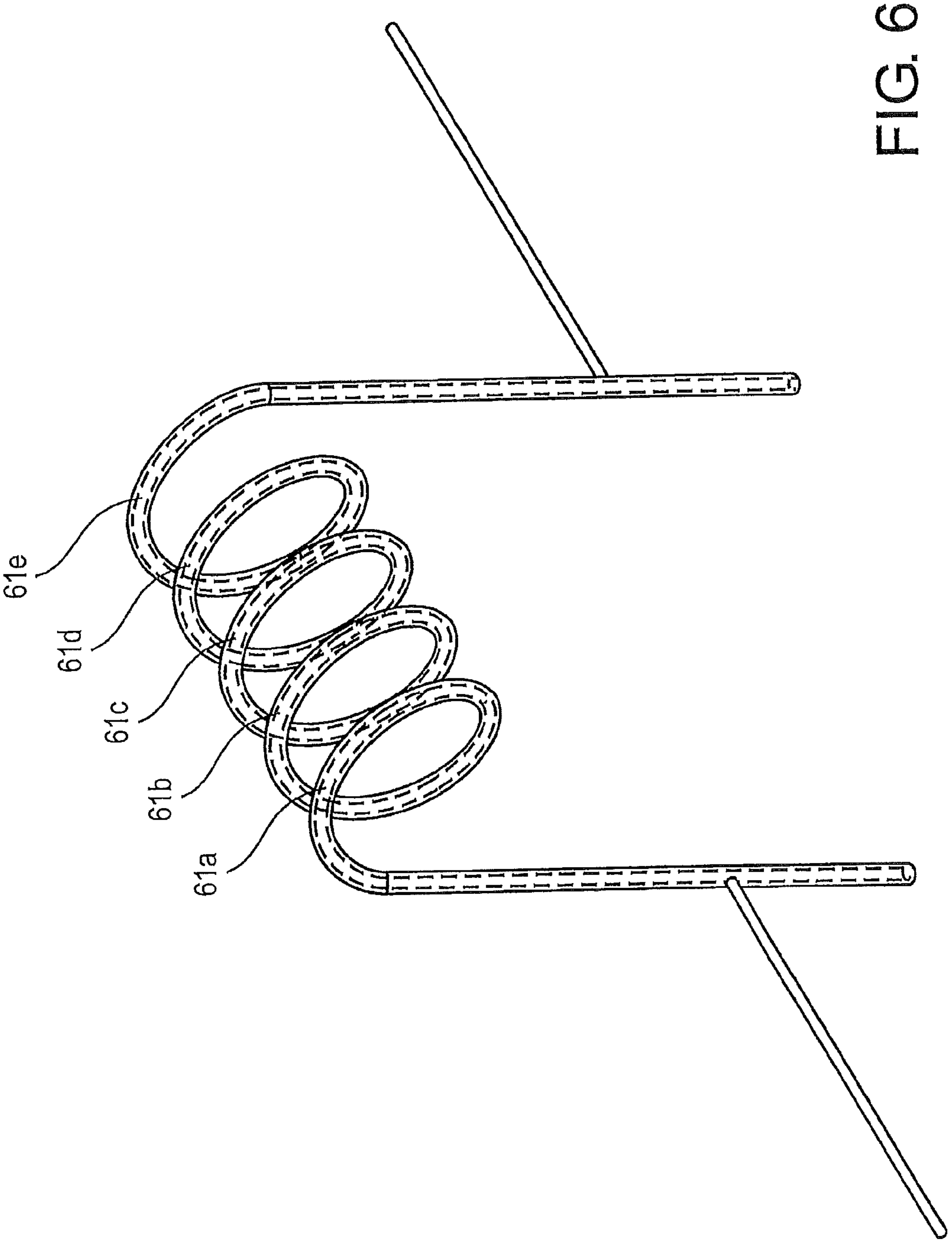

Additional embodiments of the bent capillary tube are schematically shown with reference to FIGS. 5 and 6. The bent capillary tube of FIG. 5 includes multiple bends 51*a*, 51*b*, 51*c*, preferably have a single outlet along the centermost bend 51*b*. The bent capillary tube of FIG. 6 includes a coiled tube having multiple bends 61*a*, 61*b*, 61*c*, 61*d*, 61*e*, preferably have a single outlet in the centermost bend 61*c*.

The bent capillary tube arrangement is designed to accommodate a variety of liquid flow rates through the capillary tube, is highly energy efficient and provides a compact arrangement. In inhaler applications, the heating zones of the capillary tube can be 5 to 40 millimeters long, or more preferably 10 to 25 millimeters long, and the inner diameters of the tube can be 0.1 to 0.5 millimeters, or more preferably 0.1 to 0.2 millimeters. In implementing the capillary heater in an inhaler, the bent capillary tube arrangement is preferably insulated and/or isolated from ambient air and the vapor emitted from the capillary tube. For example, a body of insulating material could be used to support the bent capillary within a mouthpiece such that the vapor exiting the capillary tube does not contact the outer surface of the capillary tube.

The direction of discharge from the capillary is disclosed in FIG. 3 as being oriented in a direction within the general plane of the capillary away from the end of portions of the capillary. In the alternative, the discharge may instead be in a direction within the general plane of the capillary toward the end of portions of the capillary or in a direction outside of the general plane defined by the capillary, such as a direction that is orthogonal to the general plane defined by the capillary.

While various embodiments have been described, it is to be understood that variations and modifications may be resorted to as will be apparent to those skilled in the art. Such variations and modifications are to be considered within the purview and scope of the claims appended hereto.

What is claimed is:

1. An aerosol generator in the form of a single, unitary capillary tube, the single, unitary capillary tube comprising at least one bend, fluid inlets, a single outlet along the bend, and first and second capillary passages venting to the single outlet, wherein volatilized fluid discharges from the outlet to form an aerosol; and a heating mechanism along the first and second capillary passages, and wherein the heating mechanism has a power supply and leads attached to the single, unitary capillary tube such that current passes along the bend and heats the single, unitary capillary tube, and wherein a temperature of the single, unitary capillary tube is greatest at the single outlet.

2. The aerosol generator of claim 1, wherein the fluid inlets are located at ends of the single, unitary capillary tube.

3. The aerosol generator of claim 1, wherein the single, unitary capillary tube comprises more than one bend.

4. The aerosol generator of claim 1, further comprising a source of liquid in fluid communication with the fluid inlets.

5. The aerosol generator of claim 4, wherein the source of liquid includes a first liquid and a second liquid and wherein the first liquid is different from the second liquid.

6. The aerosol generator of claim 1, wherein the single, unitary capillary tube is 5 to 40 millimeters long and has an inner diameter of 0.1 to 0.5 millimeters.

7. The aerosol generator of claim 1, wherein the single, unitary capillary tube is 10 to 25 millimeters long and has an inner diameter of 0.1 to 0.2 millimeters.

8. An aerosol generator comprising:

a single, unitary capillary tube comprising at least one bend, fluid inlets, a single outlet along the bend, and first and second capillary passages venting to the single outlet;

a heating mechanism along the first and second capillary passages, which heats the single, unitary capillary tube to a temperature sufficient to volatilize fluid in the first and second capillary passages, and wherein a temperature of the single, unitary capillary tube is greatest at the single outlet; and wherein the single, unitary capillary tube is made of electrically resistive heating material and the heating mechanism comprises a power supply and leads attached to the single, unitary capillary tube such that current passes along the bend and heats the single, unitary capillary tube.

9. The aerosol generator of claim 8, further comprising a mouthpiece.

10. The aerosol generator of claim 8, further comprising a source of fluid.

11. A method for generating an aerosol, comprising the steps of:

supplying fluid to an aerosol generator comprising a single, unitary capillary tube comprising at least one bend, first and second fluid inlets, a single outlet along the bend, and first and second capillary passages venting to the single outlet;

providing a power supply and leads attached near the first and second fluid inlets of the single, unitary capillary tube for supplying power to heat the single, unitary capillary tube along the first and second capillary passages; and heating the single, unitary capillary tube along the first and second passages to heat the fluid to a temperature sufficient to volatilize the fluid to form a volatized fluid, such that the volatilized fluid discharges from the outlet of the single, unitary capillary tube to form an aerosol, and wherein a temperature of the single, unitary capillary tube is greatest at the single outlet.

12. The method of claim 11, wherein the outlet is equidistant from the first and second fluid inlets.

13. The method of claim 11, wherein fluid is supplied to the first and second fluid inlets at identical flow rates.

14. The method of claim 11, wherein fluid is supplied to each of the fluid inlets at different flow rates.

15. The method of claim 11, wherein identical fluids are supplied to the first and second fluid inlets.

16. The method of claim 11, wherein different fluids are supplied to the first and second fluid inlets.

17. The method of claim 11, wherein a liquid is supplied to the first fluid inlet and a gas is supplied to the second fluid inlet.

18. A method of generating an aerosol comprising:

discharging a volatilized system from a single location along a single, unitary capillary tube having first and second capillary passages venting to the single location by introducing a volatile liquid into each of opposite end portions of the single, unitary capillary tube and volatilizing at least a portion of the liquid prior to the discharging step;

providing a power supply and leads attached near each of the opposite end portions of the single, unitary capillary tube for supplying power to heat the single, unitary capillary tube along the first and second capillary passages; and wherein the discharging is from the single location along an arcuate portion of the single, unitary capillary tube, and wherein the volatilizing includes heating the volatile liquid along the first and second capillary passages, and wherein a temperature of the single, unitary capillary tube is greatest at the single location.

19. An aerosol generator in the form of a single, unitary capillary tube, the capillary tube comprising a single bend, a first fluid inlet located at a first end and a second fluid inlet located at a second end of the single, unitary capillary tube comprising the single bend, a single, common outlet along the single bend, and wherein the single, common outlet is spaced apart from and in communication with the first and second fluid inlets, and wherein volatilized fluid discharges from the single, common outlet to form an aerosol;

a source of liquid in fluid communication with the first and second fluid inlets; and a heating mechanism having a power supply and leads attached near the first and second ends of the single, unitary capillary tube, and wherein a temperature of the single, unitary capillary tube is greatest at the common outlet.

20. The aerosol generator of claim 19, wherein the single, common outlet is equidistant from the first and second fluid inlets.

* * * * *